(12) United States Patent
Lal

(10) Patent No.: US 10,810,384 B2
(45) Date of Patent: Oct. 20, 2020

(54) BIOMETRIC THIN CARD READER WITH ENERGY HARVESTING

(71) Applicant: Geegah LLC, Ithaca, NY (US)

(72) Inventor: Amit Lal, Ithaca, NY (US)

(73) Assignee: Geegah LLC, Ithaca, NY (US)

( * ) Notice: Subject to any disclaimer, the term of this patent is extended or adjusted under 35 U.S.C. 154(b) by 0 days.

(21) Appl. No.: 16/299,974

(22) Filed: Mar. 12, 2019

(65) Prior Publication Data

US 2019/0278953 A1    Sep. 12, 2019

Related U.S. Application Data

(60) Provisional application No. 62/641,496, filed on Mar. 12, 2018.

(51) Int. Cl.
*G06K 7/06* (2006.01)
*G06K 7/00* (2006.01)
*A61B 5/1172* (2016.01)

(52) U.S. Cl.
CPC .......... *G06K 7/0021* (2013.01); *A61B 5/1172* (2013.01)

(58) Field of Classification Search
CPC .............................. A61B 5/1172; G06K 7/0021
See application file for complete search history.

(56) References Cited

U.S. PATENT DOCUMENTS

| | | | | |
|---|---|---|---|---|
| 5,679,007 A | * | 10/1997 | Potdevin | G06K 7/0021 439/76.1 |
| 9,888,337 B1 | * | 2/2018 | Zalewski | H04L 67/10 |
| 2002/0007459 A1 | * | 1/2002 | Cassista | H04M 1/67 726/3 |
| 2009/0270045 A1 | * | 10/2009 | Flaherty | G06Q 20/3278 455/73 |
| 2010/0045455 A1 | * | 2/2010 | Mazzolini | G08B 13/14 340/521 |
| 2011/0291428 A1 | * | 12/2011 | Milton-Benoit | E05B 47/0692 292/228 |

* cited by examiner

*Primary Examiner* — Thien M Le
(74) *Attorney, Agent, or Firm* — Bond, Schoeneck & King PLLC; Erin Phillips

(57) ABSTRACT

A thin card reader (TCR) designed to reduce card-not-present fraud, in credit card transactions, and other applications where security verification is needed in remote locations. The TCR is powered by external RF power, or through a battery. Further, the TCR uses energy from an energy harvester, which converts the mechanism energy used to insert the credit card into the TCR. Energy harvesting allows the TCR to be a self-powered device, alleviating the need to charge the TCR or connect a cable thereto. TCR shifts the burden of the electronics from the card to the TCR, reducing the cost of credit cards with a biometric sensor. One TCR can be used per consumer (with many cards), reducing costs and resulting in substantial savings. The TCR also allows remote enrollment of biometrically enabled credit cards where the new card can be entered into a TCR when placed in a self-enrollment mode.

20 Claims, 16 Drawing Sheets

BIOMETRIC THIN CARD READER WITH ENERGY HARVESTING

CROSS-REFERENCE TO RELATED APPLICATIONS

This application claims priority to U.S. Provisional Patent Application Ser. No. 62/641,496 filed on Mar. 12, 2018 and entitled "Thin Card Reader," the entirety of which is incorporated herein by reference.

BACKGROUND OF THE INVENTION

1. Field of the Invention

The present invention is directed generally to a credit card processing device and, more particularly, to a thin card reader for reducing fraud and which is powered by an on-board energy harvester.

2. Description of Related Art

Card-not-present (CNP) fraud includes telephone, Internet, and mail-order transactions where the cardholder does not physically present the card to the merchant. Most CNP fraud involves the use of card details that have been obtained through skimming, hacking, email phishing campaigns, telephone solicitations or other methods. The card details are then used to facilitate fraudulent transactions. Although EMV (Euro Mastercard VISA) chips deal effectively with counterfeit fraud, the chips do not provide protection against CNP fraudulent transactions. With the migration to EMV for card-present transactions, fraudsters shift their focus to other channels, such as CNP transactions.

Fingerprint sensors, and other biometric indictors on credit cards have the potential to reduce fraud but only when the user is near a reader connected to a controlled security environment, such as teller machine or a sales point in stores. When the card is not near a secure reader, fraud can occur as a person not owning the card has access to the codes to make the purchase. When someone uses the credit card away from a connected card reader, fraud can occur as the person can enter the card information and the code at the back of the card, even though that person may not be the owner of the card. It is possible to have credit cards that have been realized which include all electronics for processing fingerprint sensors that communicate with an external electronic device using power transmitted using RF interfaces. The approach of more electronics on the credit card increases the cost of the credit card that is typically burdened by the card issuing bank.

Therefore, there is a need for a device that can reduce card-not-present fraud, in credit card transactions, and other applications where security verification is needed in remote locations. Many previous readers, with integrated biometric sensors, require a cable connected to a computing system to power the device, which makes the use of the device unwieldy. A device that can be untethered, can be self-powered or powered through RF, can provide the convenience of using the card easily.

SUMMARY OF THE INVENTION

As most credit cards and identity cards are typically stored in personal wallets, a path to ready adoption of biometrically enabled transactions and identification steps would be to include the card reader within the wallet itself, with minimal impact on holding space within the wallet. The user, who is used to taking out a wallet out of the pocket or from a bag, to take out a credit card, can insert the card back into the wallet where the reader is integrated, minimally impacting lifestyle while providing greater security. The wallet integrated thin card reader can also solve a major problem with biometric enabled credit cards, namely that of enrollment of new fingerprint card to a new user. At present the enrollment requires a separate reader or the user has to go to a location such as bank to enroll a new credit card. The thin card reader can be placed in an enrollment mode for a new credit card to store the fingerprint data on the credit card, without the need for going to a bank or using a separate device for enrollment. The dual mode of enrollment, and as a transaction reader, within the control of the user, allows the thin card reader to provide added security enabled by biometric fingerprint sensors.

The present invention is a thin card reader (TCR) designed to reduce card-not-present fraud, in credit card transactions, and other applications where security verification is needed in remote locations. Hence, the TCR provides a personal reader that takes the credit card and only approves the transaction if a biometric sensor on the credit card is authenticated. If a potential fraud is attempted by a person with a stolen card, their fingerprint would not match the fingerprint data stored on the credit card. The TCR can be powered by an external RF power source or through a battery. Further, the TCR can use energy generated from an energy harvester, which converts the mechanism energy used to insert the credit card into the TCR. Energy harvesting can allow the TCR to be a self-powered device, alleviating the need to charge the TCR or connect a cable thereto. Compared to a single credit card with all electronics and RF communications, the TCR allows the shifting of the burden of the electronics from the card to the TCR, enabling a reduction in the cost of the credit card with a biometric sensor. Since consumers typically hold many credit cards, the reduction in costs from having one TCR per user can result in substantial savings to banks that issue the credit cards, usually at no cost to the user.

According to one aspect, the thin card reader includes a rectangular housing having a top section connected to a bottom section. The housing has a first end with a slot extending therethrough and into the housing. The thin card reader also includes a power source in the bottom section of the housing, a plurality of piezoelectric bimorph springs extending from the power source toward the first end of the housing, and a hard stop barrier between at least two of the plurality of piezoelectric bimorph springs. The plurality of piezoelectric bimorph springs are movable between an uncompressed state, a first distance from the first end of the housing, and a compressed state, a second distance from the first end of the housing. The second distance is between the first end of the housing and the hard stop barrier. The thin card reader additionally includes an electronics board connected to the top section of the housing and electrically connected to the power source, and one or more electrodes connected to the top section of the housing. The electronics board is configured to transmit and receive a wireless signal consisting of encrypted identity tokens.

According to another aspect, the thin card reader includes a housing having a top cover plate connected to a bottom cover plate. The housing has a first end with a slot extending therethrough and into the housing. The thin card reader also includes a piezoelectric bimorph layer extending from a second end of the housing between the top cover plate and the bottom cover plate, a first spacer between the top cover plate and the piezoelectric bimorph layer at the second end of the housing, a second spacer between the bottom cover plate and the piezoelectric bimorph layer at the second end of the housing, a spacer rod connected to the first spacer and a spring connected to the first spacer and extending along the spacer rod, and a spacer connected to the spring. The spacer is movable along the spacer rod and the spacer is movable between an uncompressed state and a compressed state. In the compressed state, the piezoelectric bimorph layer bends downward toward the bottom cover plate, generating a charge stored in an electronics board at the bottom cover plate.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
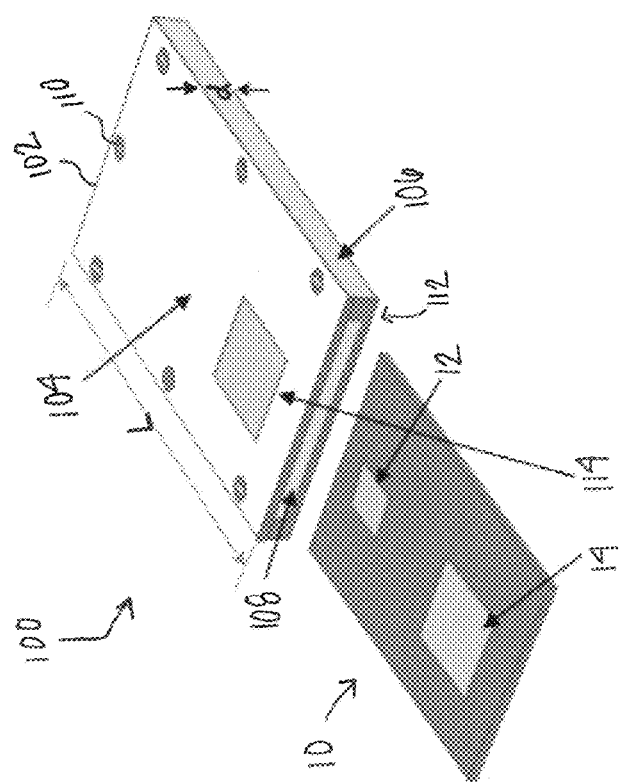
FIG. 1 is a perspective view schematic representation of a thin card reader device, according to an embodiment.

Referring now to the figures, wherein like reference numerals refer to like parts throughout, FIG. 1 shows a thin planar device 100, hereinafter referred to as a "thin card reader" (TCR). The TCR 100 can read credit cards, or similar electronic identification cards. A card 10 (hereinafter meaning a conventional credit card or any other similar electronic identification card) can be inserted into TCR 100 such that the information on the card 10 can be transmitted externally wirelessly. FIG. 1 shows an exemplary embodiment of a TCR 100 and a card 10. The TCR shown in FIG. 1 comprises a rectangular housing 102. The housing 102 is preferably rectangular to accommodate the rectangular shape of most conventional credit cards; however, a housing 102 having a different configuration can be used.

Still referring to FIG. 1, in the depicted embodiment, the housing 102 comprises a top section 104 attached to a bottom section 106 with a slot 108 (or inner volume) therebetween. In an embodiment, the slot 108 is formed in a recess (not shown) in the bottom section 106. In an alternative embodiment, a third spacer layer (not shown) is positioned and attached between the top section 104 and the bottom section 106 to form a gap for the card 10 to be inserted. The top section 104 and the bottom section 106 can be formed in the same material via molding or can be separate plates connected via adhesive bonding and/or conventional connectors 110 (e.g., screws and mechanical linkages), which is shown. The TCR 100 has a length L and a depth (i.e., thickness) d. In a preferred embodiment, the length L is approximately 10 cm and the depth d is approximately 3 mm.

The slot 108 in the embodiment shown in FIG. 1 is extends through a first end 112 of the housing 102 and is rectangular and sized/configured to receive the card 10. In the depicted embodiment, the card 10 comprises an EMV chip 12, which has become a standard verification feature of conventional credit cards. The card 10 may also comprise a first biometric sensor 14, such as a fingerprint sensor, as shown. As the card 10 is inserted by the user by holding the card with his/her fingers, it is natural for the first biometric sensor 14 to be a fingerprint sensor. In the embodiment shown in FIG. 1, the TCR 100 comprises a second biometric sensor 114 (e.g., fingerprint sensor) on the top section 104 of the housing 102. The second biometric sensor 114 can be used to authenticate that the finger used for the first biometric sensor 14 on the card 10. Although the second biometric sensor 114 is shown on the top section 104 of the housing, it can be similarly applied to the bottom section 106 in the alternative. Another implementation is to only use the biometric sensor on the TCR body, even with a credit card without a biometric sensor. In this embodiment, the card can be less inexpensive, and utilizes the biometric on the reader to validate the identity. This solution addresses the private security challenge of storing biometric data on external readers, where users do not like to place their fingerprints on someone else's device. In the TCR solution presented here, the fingerprint data is stored on TCR that is always with the user. In the case, the wallet is stolen, and the thief can get the fingerprint data, and this can be avoided by using tamper resistant memory, as is done on memory used to store fingerprint data on biometrically enabled credit cards.

Figure 2:
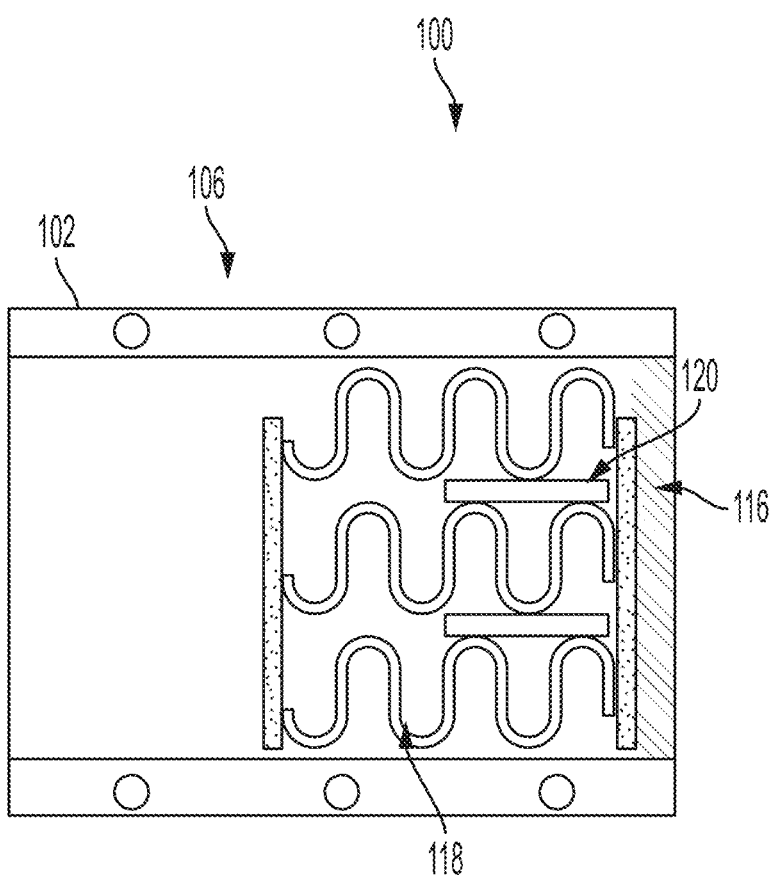
FIG. 2 is a bottom sectional view schematic representation of the thin card reader device, according to an embodiment.

Turning now to FIG. 2, there is shown a bottom sectional view schematic representation of the TCR 100, according to an embodiment. The bottom section 106 of the housing 102 comprises a power source 116. In the depicted embodiment, the power source 116 includes a battery, a capacitor, or other known power source electronics. In FIG. 2, the power source 116 is a thin battery, such as a thin lithium ion battery. The thin battery 116 can be placed in a gap between the top section 104 and the bottom section 106, or can be attached to the top section 104 and the bottom section 106. The bottom section 106 additionally comprises piezoelectric lateral bimorph serpentine springs 118 extending at least partially across the length L of the bottom section 106. In the depicted embodiment, the springs 118 are separated by one or more hard stops 120. The hard stops 120 are barriers that define the extent of the motion of the bimorph spring structure (i.e., springs 118).

Figure 3:
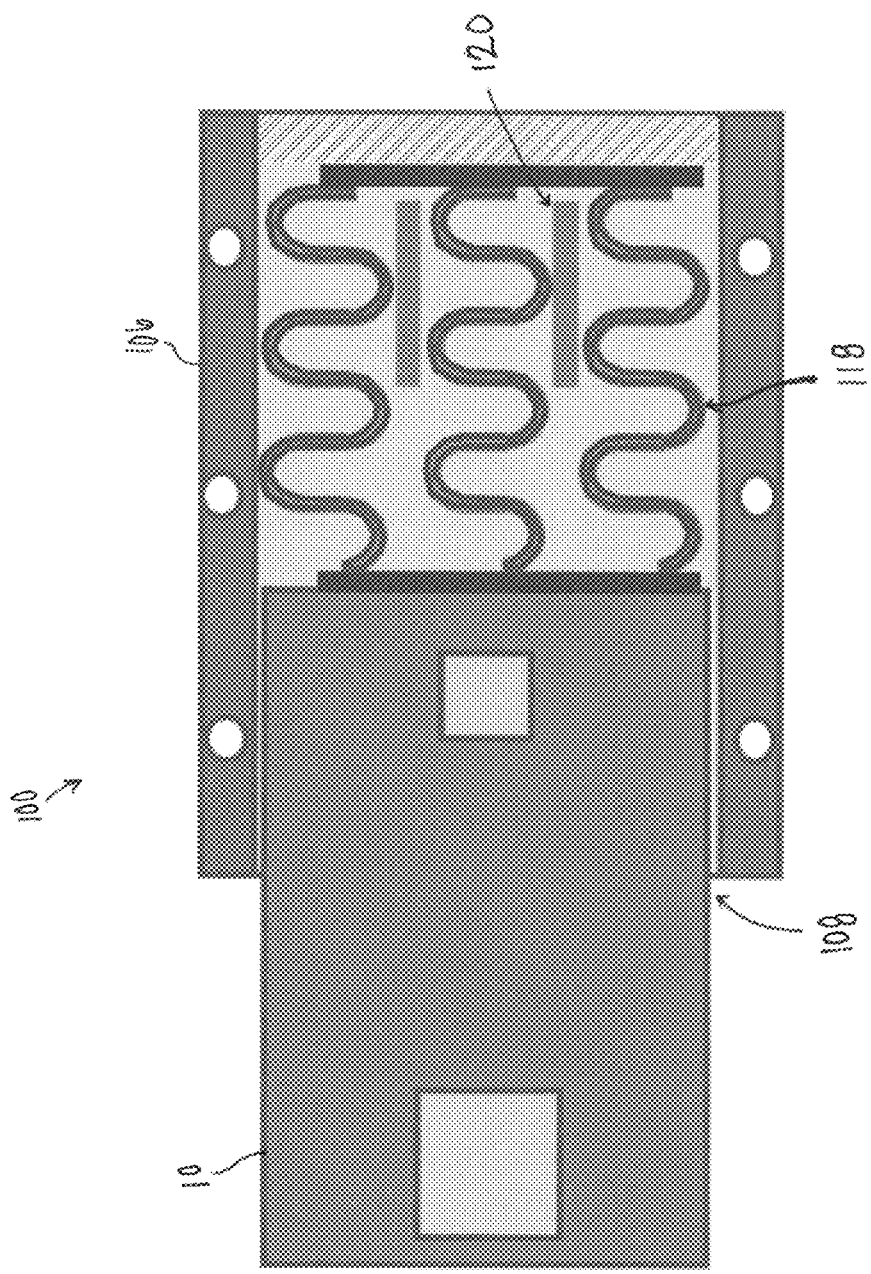
FIG. 3 is a bottom sectional view schematic representation of the thin card reader device in an uncompressed state, according to an embodiment.
Figure 4:
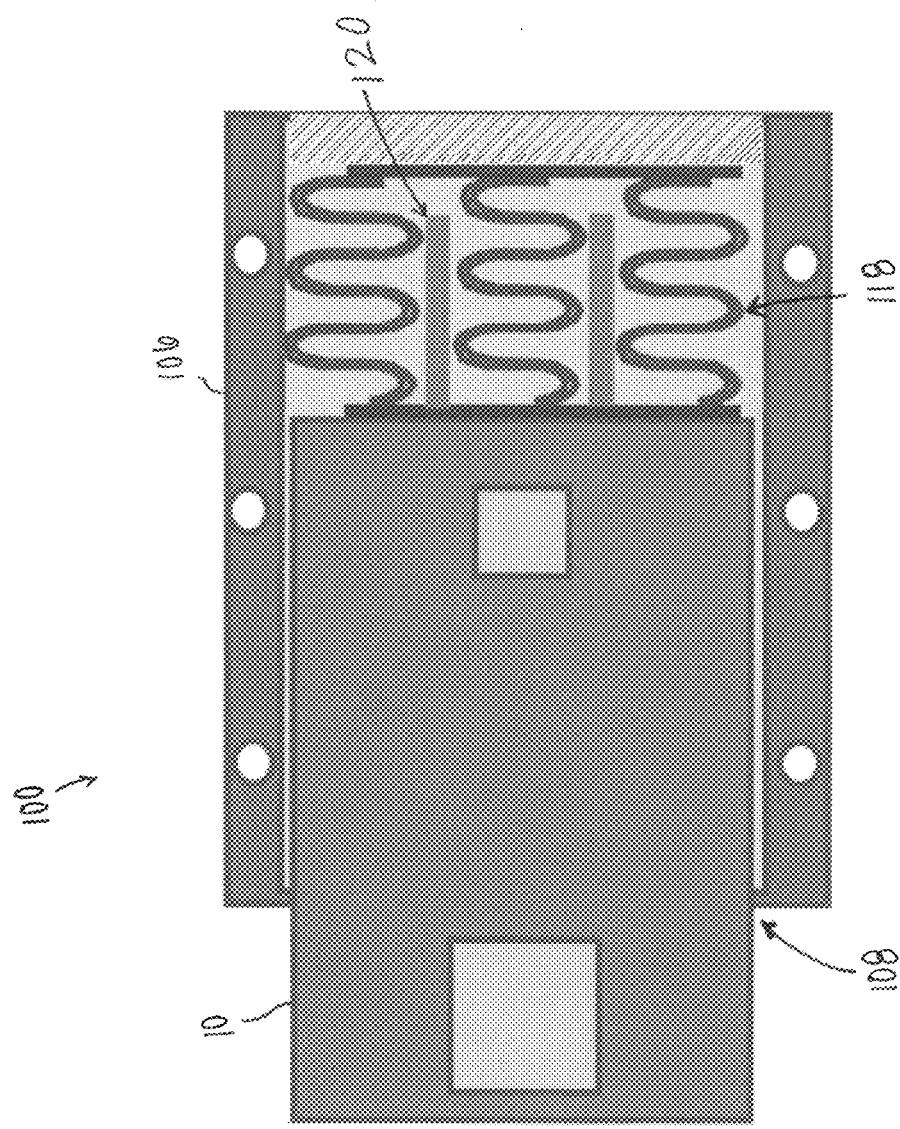
FIG. 4 is a bottom sectional view schematic representation of the thin card reader device in a compressed state, according to an embodiment.

Referring now to FIGS. 3 and 4, there are shown bottom sectional views schematic representations of the TCR 100 in an uncompressed state and a compressed state, respectively, according to an embodiment. In FIG. 3, the card 10 has been inserted into the slot 108 of the TCR 100. In the uncompressed state, as shown in FIG. 3, the card 10 has been inserted a first distance into the slot 108, just far enough that the springs 118 remain fully extended and uncompressed. In the compressed state, as shown in FIG. 4, the card 10 has been inserted a second distance into the slot 108 such that the springs 118 are compressed. As shown in FIG. 4, the hard stops 120 limit the compression on the springs 118. Thus, the card 10 can only be inserted up to the hard stops 120 and the hard stops 120 represent the second distance.

Figure 15:
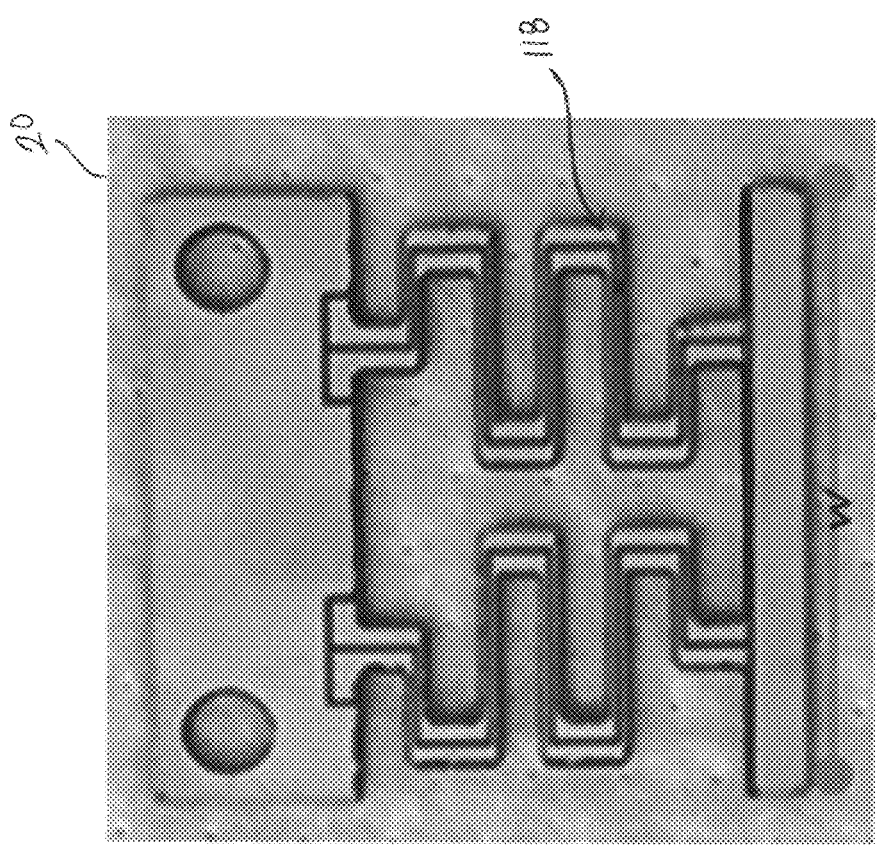
FIG. 15 is a single PZT (Lead Zirconate Titanate Oxide) plate used to form piezoelectric lateral bimorph serpentine springs by laser cutting.
Figure 16:
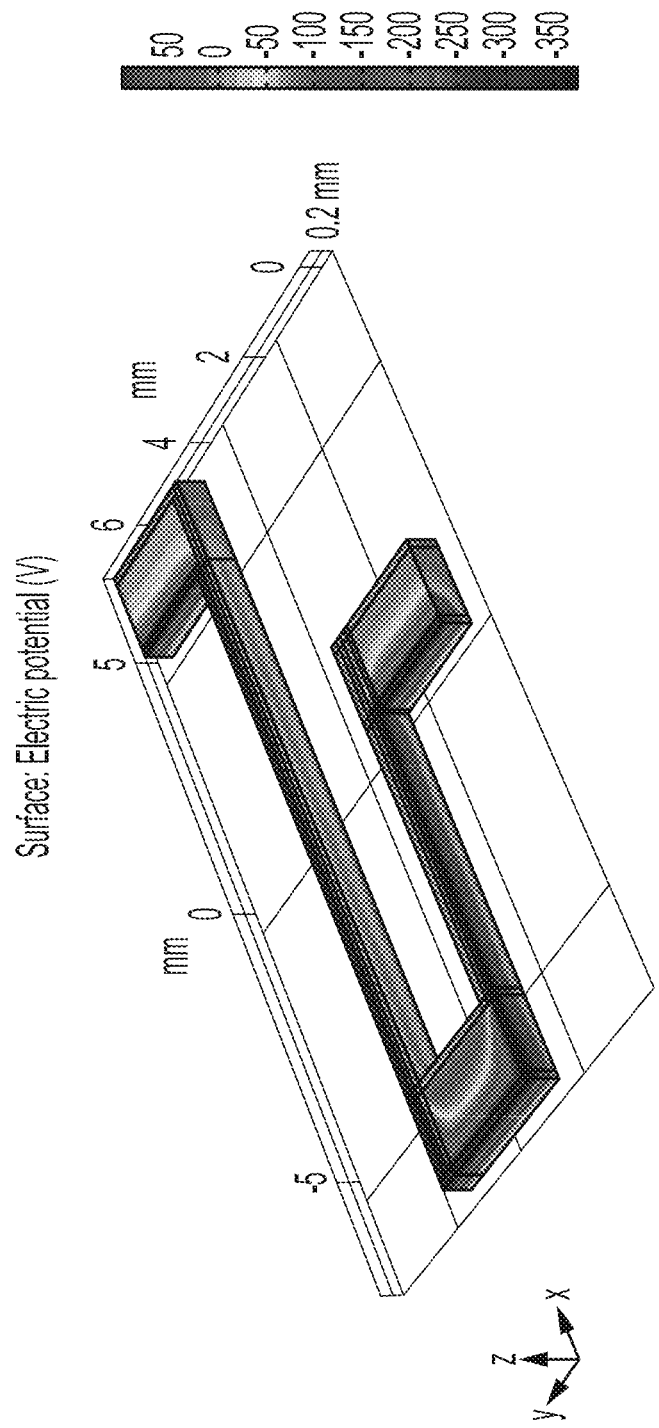
FIG. 16 is a graph showing the electric potential of the piezoelectric lateral bimorph serpentine springs.

Every time the TCR 100 is in the compressed state and the springs 118 are compressed, the springs 118 generate electricity. Laser cutting can be used to form the piezoelectric lateral bimorph serpentine springs 118 from a single PZT (Lead Zirconate Titanate Oxide) plate 20 that is approximately 0.3-0.5 mm thick, as shown in FIG. 15. (In FIG. 15, the PZT plate 20 has a width w, which is approximately 25.4 mm). These springs 118 generate charge and voltage across the total capacitance of the spring 118 itself and a load capacitor. The springs 118 can be designed to have spring constants and displacements to generate energy in the range of ~1-10 mJoules of energy to satisfy the power requirements of the TCR 100, by amplifying strains in the beams as needed. In an embodiment, the power consumption of the TCR 100 is within the range of 1-5 mW for a period of 1-2 seconds, corresponding to ∥1-10 mJoules of energy.

The voltage on the capacitance can be conditioned using limiting diodes, inductors, capacitors to generate power supply suitable to drive the electronics needed to drive the first and second biometric sensors 14, 114 and analyze the card data and/or biometric sensor data. Note that the serpentine structure of the springs 118 shown in FIGS. 2-4 and 15 for the lateral piezoelectric transducers shown here is exemplary. Many other structures, shapes, and configurations can be designed and used that maximize voltage output versus current output, and can be segmented to provide different power levels for different purposes in the TCR 100.

Figure 5:
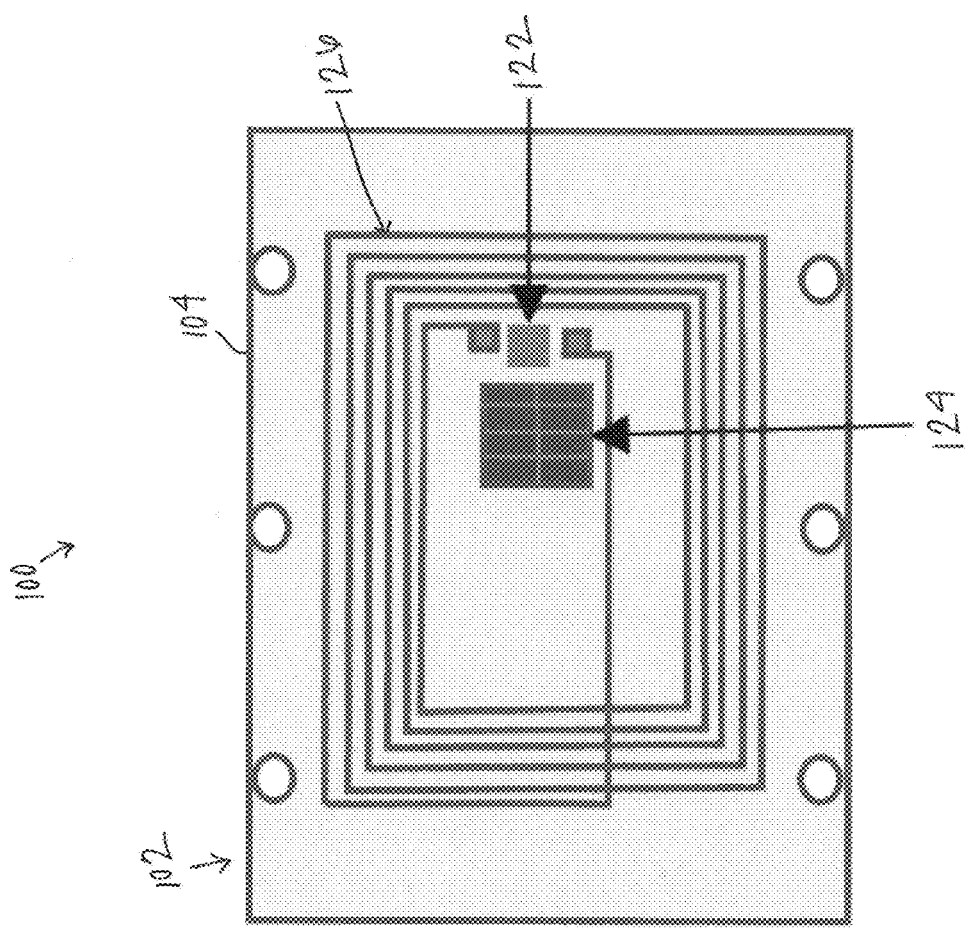
FIG. 5 is a top sectional view schematic representation of the thin card reader device, according to an embodiment.
Figure 6:
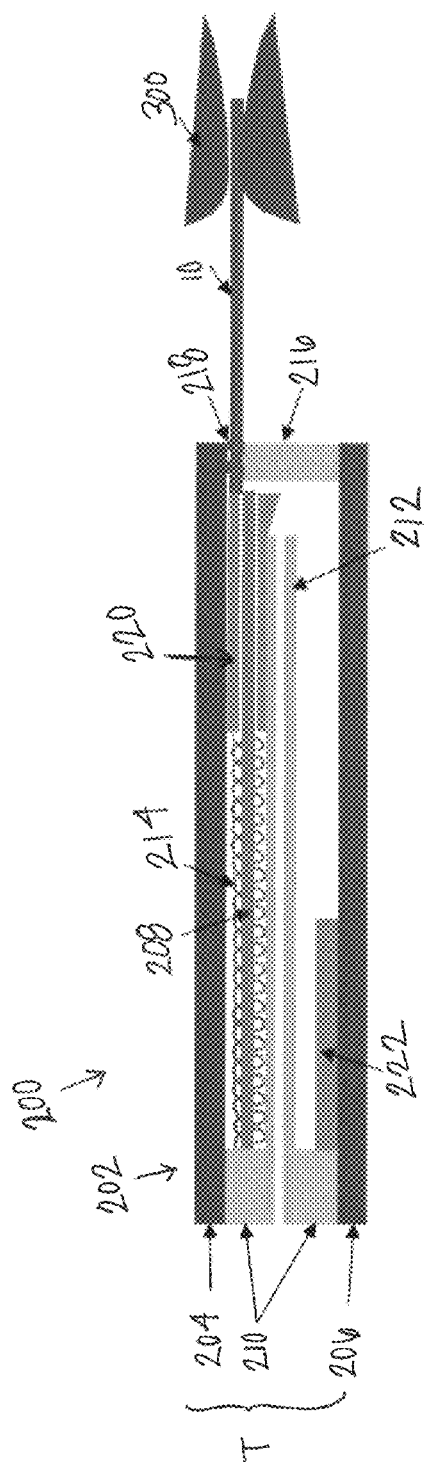
FIG. 6 is a side sectional view schematic representation of the thin card reader device, in the uncompressed state, according to an alternative embodiment.

Turning now to FIG. 5, there is shown a top sectional view schematic representation of the TCR 100, according to an embodiment. The top section 104 of the housing 102 comprises an integrated circuit (IC) 122 for connecting to the EMV chip 12 and the first and second biometric sensors 14, 114. The top section 104 further comprises one or more electrodes 124 for interfacing with and reading the EMV chip 12. The electrodes 124 can be attached to or integrated within the top section 104 of the housing 102. The electrodes 124 are positioned within the top section 104 such that they contact the electrical pads (not shown) on the card 10 when the card 10 is inserted in the slot 108 to the second distance. Any gap or space between the card 10 and the electrodes 124 in the top section 104 must be small enough such that mechanical contact from the top section 104 (and electrodes 124) is sufficient to touch the card 10 with friction forces.

Once the electrodes 124 are in contact with the electrical pads (not shown) on the card 10, the power from the power source 116 (e.g., battery) is used to process the card information ("card data") and biometric sensor data (e.g., fingerprint) from the first and/or second biometric sensors 14, 114. The biometric sensor data is used to determine that the person associated with the card 10 (and card data) is the same person represented by the biometric sensor data. In an embodiment, an algorithm to identify the biometric sensor data is processed with an on-chip low power microcontroller (shown as part of IC 122). In another embodiment, the biometric sensor data is being transferred to a receiver (not shown) with encryption.

A wireless or wired interface can be used to transmit the card data and/or biometric sensor data using wireless protocols such as Wi-Fi, Bluetooth, near field communications (NFC) or other proprietary radio protocol. This allows for a commonly available radio protocols to be used which are not blocked by smartphone manufacturers. As the card data and/or biometric sensor data transmitted and received can contain secure data that should not be available to adversarial listeners, the TCR 100 (via the microcontroller 122) can encode the data, as mentioned above, using approaches such as stored or transmitted keys, or Physically Unclonable Features (PUF) read out using sonic interrogation of the card 10 with unique ultrasonic features, etc. The top section 104 of the TCR 100 may also comprise a printed circuit board (PCB) (not shown) comprising a coil 126, IC 122, and electrodes 124. The PCB (not shown) can be a flexible PCB attached to a rigid top section 104. Alternatively, the top section 104 can be one PCB covered with an insulating layer to protect the board from external boundary conditions.

Still referring to FIG. 5, the top section 104 of the housing 102 is shown comprising the coil 126. In the depicted embodiment, the coil 126 is a radio frequency (RF) coil used to transmit the card data and/or biometric sensor data via RF communication. The RF coil 126 can also be used to also harvest RF power to charge the on-board power source 116 (e.g., battery). In this approach for energy generation, the RF coil 126 is an energy harvester that takes the mechanical energy used to push the card 10 into the reader and converts into electricity using transducers such as piezoelectric or electromagnetic generators.

The act of inserting the card 10 generates sufficient energy to power the entire card 10 readout operation. In this embodiment, the TCR 100 can have a self-powering capability, eliminating any battery 116 (or capacitor) to store energy, allowing for an even smaller TCR 100. In an embodiment, the harvested power can also be transmitted through the RF coil 126 to charge the battery 116. In yet another embodiment, the TCR 100 may also include a display (not shown) or one or more indicators (not shown) for indicating power and successful reading of the card 10. In an alternative embodiment, the springs 118 can also serve as vibration energy harvester such that as the user walks with the TCR 100 on the body (e.g., in the wallet or a purse), the walking motion would cause the springs 118 to vibrate, generating electricity charging the on-board battery 116.

Turning briefly to FIGS. 6-11, there are shown various views schematic representations of a TCR 200, according to an alternative embodiment. In the depicted embodiment, the TCR 200 comprises a housing 202 with a thickness T, which is approximately 7 mm. The housing 202 includes a top cover plate 204 and a bottom cover plate 206, both made of plastic materials and formed from 3D printing. The top cover plate 204 and the bottom cover plate 206 are separated by one or more spacers 210. In the depicted embodiment, the TCR 200 comprises a pair of spacers 210 on either side of a PZT bimorph 212.

Figure 7:
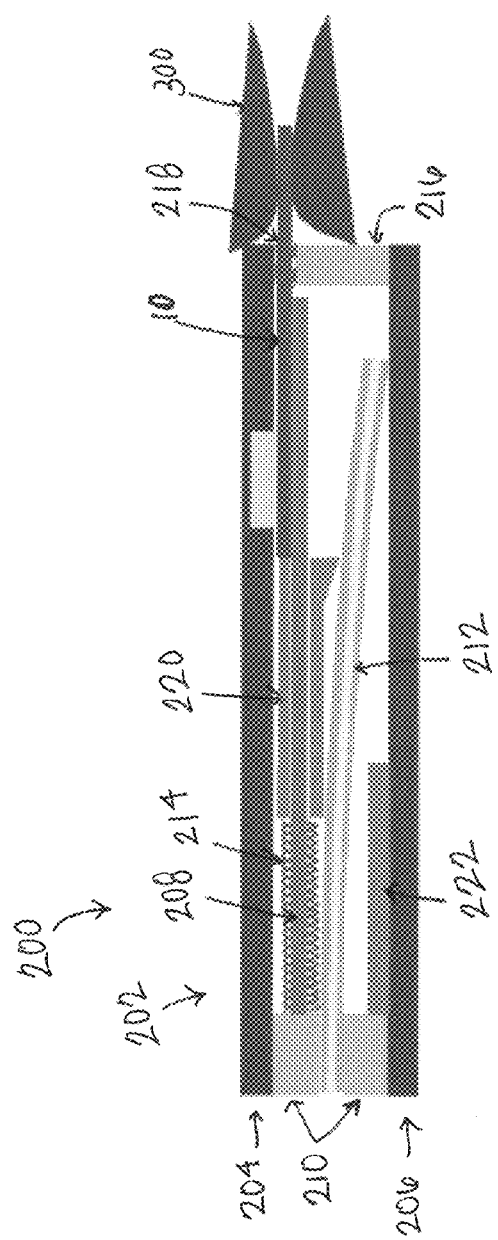
FIG. 7 is a side sectional view schematic representation of the thin card reader device, in the compressed state, according to an alternative embodiment.
Figure 8:
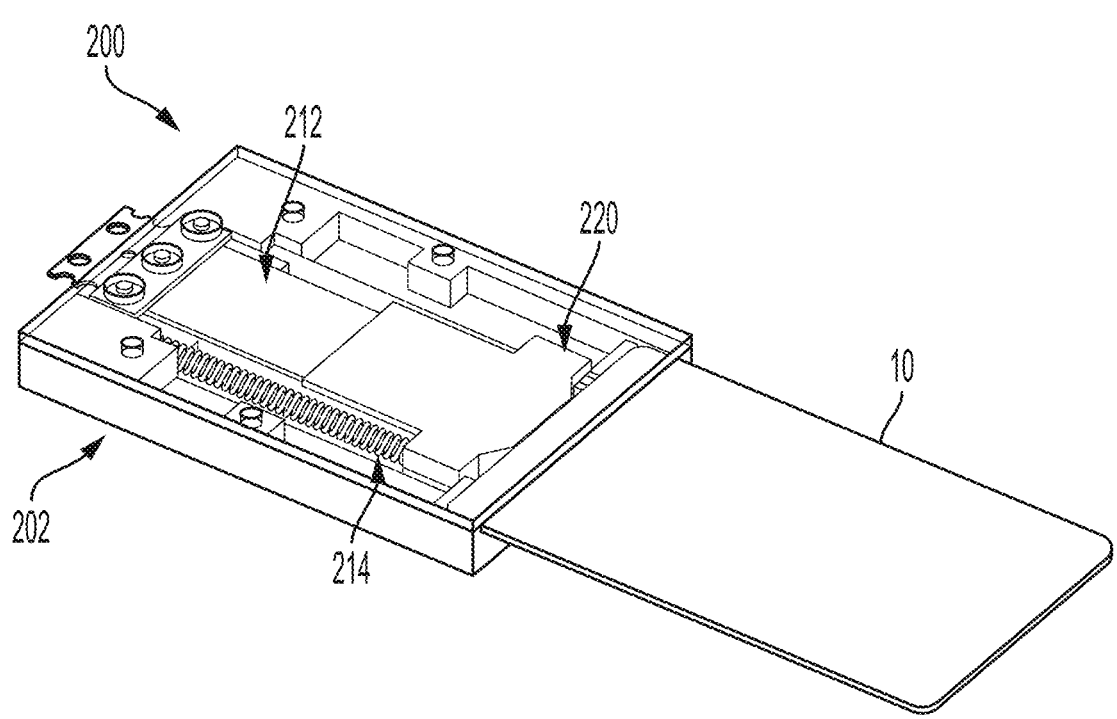
FIG. 8 is a top perspective view schematic representation of the thin card reader of FIG. 6.
Figure 9:
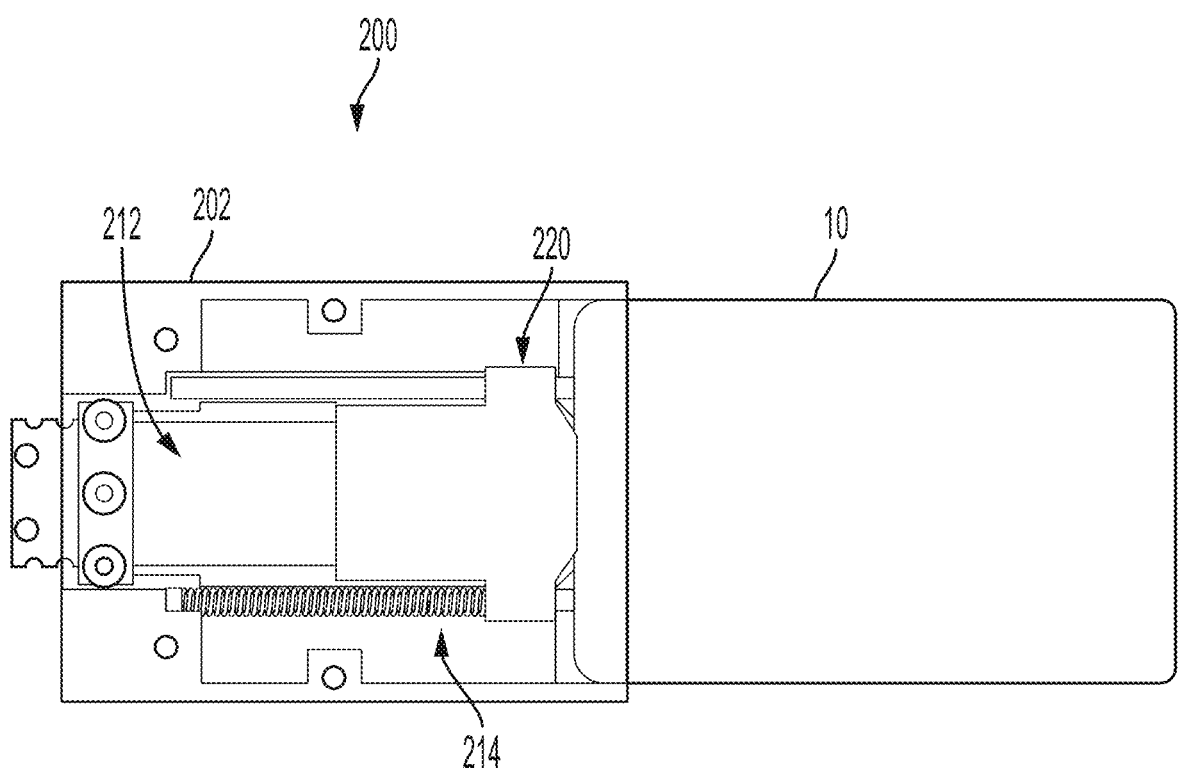
FIG. 9 is a top view schematic representation of the thin card reader of FIG. 6.
Figure 10:
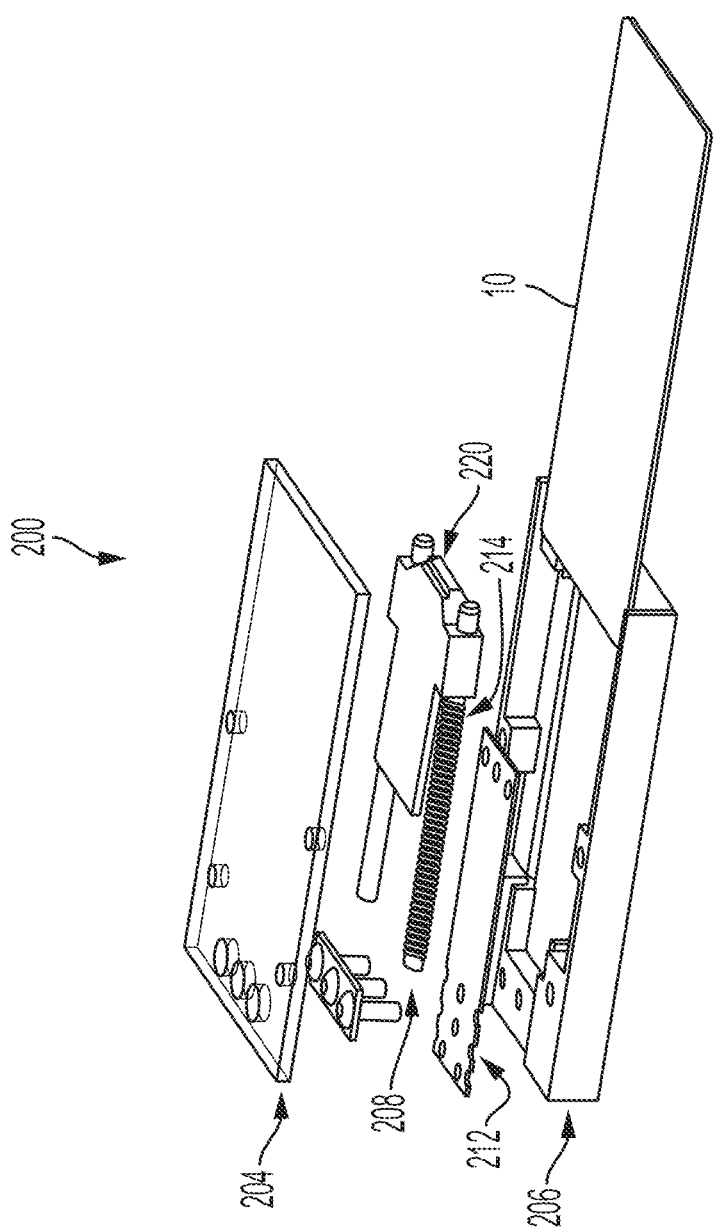
FIG. 10 is an exploded view schematic representation of the thin card reader of FIG. 6.
Figure 11:
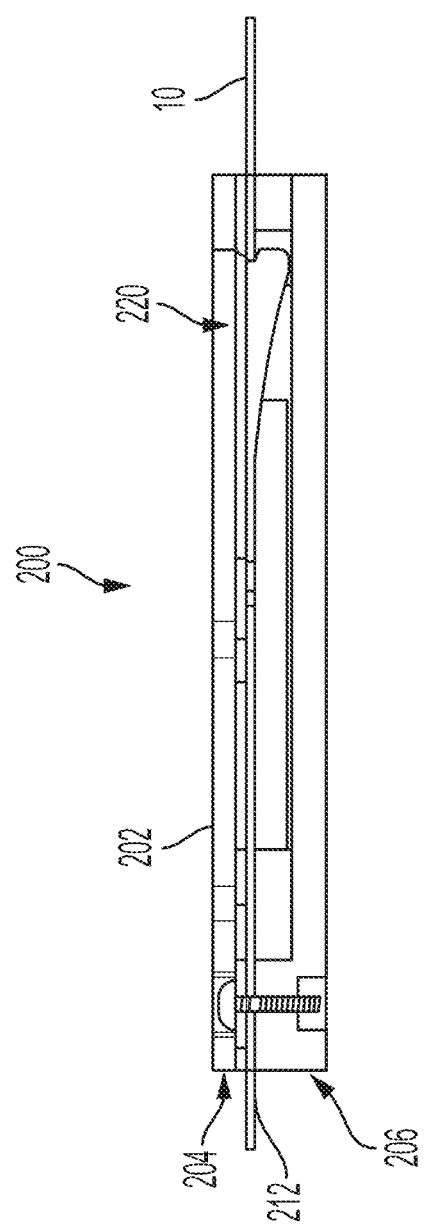
FIG. 11 is a side view schematic representation of the thin card reader of FIG. 6.

The TCR 200 also comprises a slider rod 208, which is a rod that is anchored in at least one or the spacers 210. A spring 214 pushes a slider 220, which is movably attached around the slider rod 208, so that the slider 220 rests at a front plate 216 of the housing 202. When the credit card 10 being held by fingers 300 is inserted into a slot 218 in the front plate 216 of the housing 202, it pushes the slider 220 back toward the spacers 210, sliding or otherwise moving along the slider rod 208, and also bending the PZT bimorph 212 downward toward the bottom cover plate 206. This generates charge that is stored in an electronics board 222 that consists of the storage capacitor, rectifier, and electronics to process the data on the card 10, read the biometric sensor (not shown), and transmit the data using RF connections. Electrical connections from the bimorph 212 to the electronics board (e.g., PCB) 222 are through wires (not shown) from the bimorph 212 to the board 222. The limit of insertion can be by the length of the card 10 or when the fingers 300 come in contact with the housing 202, as shown in FIG. 7.

Figure 12:
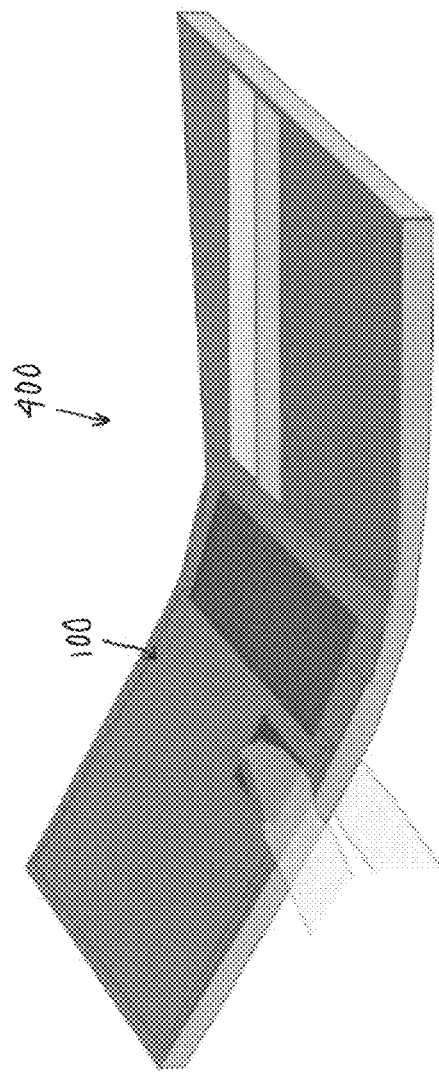
FIG. 12 is a perspective view schematic representation of the thin card reader integrated into a wallet, according to an embodiment.
Figure 13:
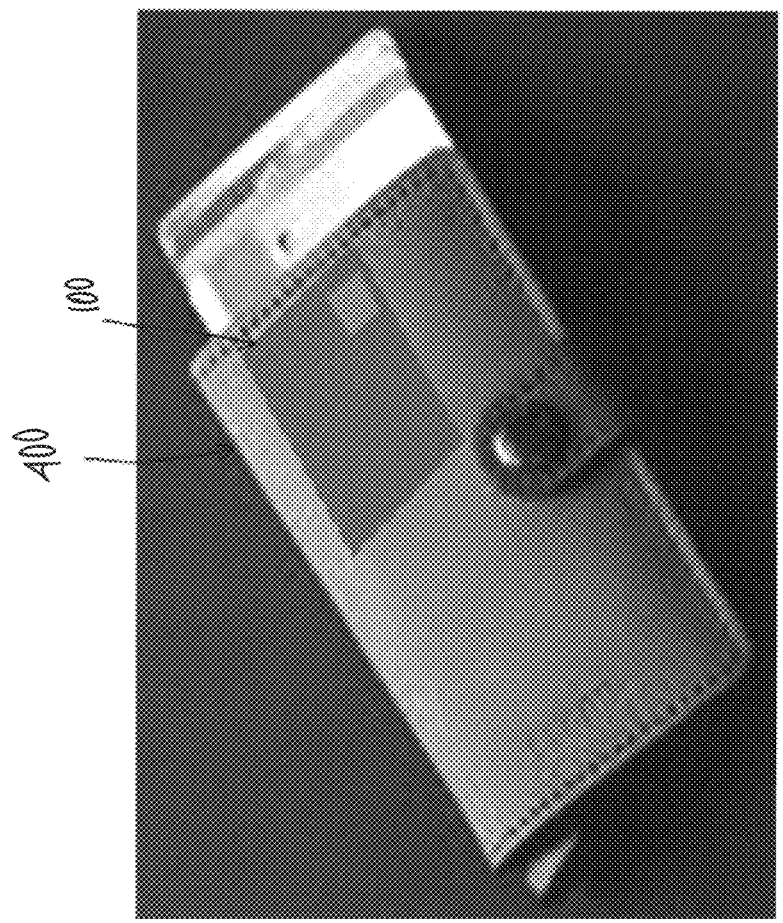
FIG. 13 is a top perspective view schematic representation of the thin card reader integrated into a wallet, according to an alternative embodiment.
Figure 14:
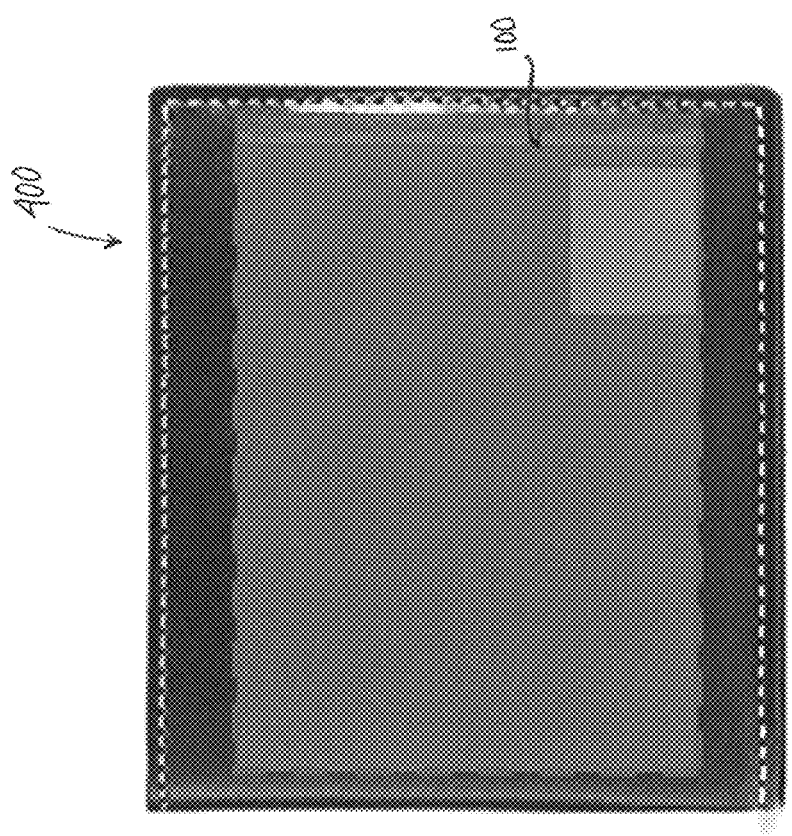
FIG. 14 is a top view schematic representation of the thin card reader integrated into a wallet, according to another embodiment.

Referring now to FIG. 12-14, there are shown various views schematic representations of the TCR 100 (or similarly, TCR 200) integrated into a wallet 400, according to an embodiment In the depicted embodiment, the TCR 100 can fit inside of a standard sized wallet 400 with minimal impact on thickness. The TCR 100 can be placed inside a wallet designed to also have a slot 108 such that it does not need to be taken out of the wallet 400. Wallets 400 are typically designed to hold credit cards, and other forms of identification such as driver licenses. The TCR 100 is also intended to be used inside wallets 400 that can go inside larger purses (not shown). Another advantage of the TCR 100 is that user almost always has to take out the card 10 from the wallet 400 to touch the first biometric sensor 14 and wave it near the smartphone or laptop. This requires motion of the arm from the wallet 400 to the smartphone and has to be close enough for NFC to work if NFC is used. However, when using the TCR 100, the user takes out the card 10 and inserts it into the same wallet 400, placed near the smartphone and/or laptop, allowing for less motion of the arms and hence would be more convenient to use.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:
1. A thin card reader, comprising:
 a rectangular housing having a top section connected to a bottom section, the housing having a first end with a slot extending therethrough and into the housing;
 a power source in the bottom section of the housing;

a plurality of piezoelectric bimorph springs extending from the power source toward the first end of the housing;

a hard stop barrier between at least two of the plurality of piezoelectric bimorph springs;

wherein the plurality of piezoelectric bimorph springs are movable between an uncompressed state, a first distance from the first end of the housing, and a compressed state, a second distance from the first end of the housing;

wherein the second distance is between the first end of the housing and the hard stop barrier;

an electronics board connected to the top section of the housing and electrically connected to the power source;

wherein the electronics board is configured to transmit and receive a wireless protocol;

one or more electrodes connected to the top section of the housing; and wherein power consumption by the electronics board is substantially similar to energy generated when moving the plurality of piezoelectric bimorph springs from the uncompressed state to the compressed state.

2. The thin card reader of claim 1, wherein the housing has a length which is approximately 10 cm.

3. The thin card reader of claim 1, wherein the housing has a depth which is less than or equal to 3 mm.

4. The thin card reader of claim 1, wherein the top section of the housing comprises a biometric sensor.

5. The thin card reader of claim 1, wherein the slot is configured to receive a credit card.

6. The thin card reader of claim 5, wherein the credit card comprises an EMV chip with an electrode pad, which is configured to transmit card data to the electronics board when the electrode pad contact the electrodes of the top section.

7. The thin card reader of claim 1, wherein the electronics board includes a radio frequency coil configured to transmit data via radio frequency communication.

8. A thin card reader, comprising:
a housing having a top cover plate connected to a bottom cover plate, the housing having a first end with a slot extending therethrough and into the housing;
a piezoelectric bimorph layer extending from a second end of the housing between the top cover plate and the bottom cover plate;
a first spacer between the top cover plate and the piezoelectric bimorph layer at the second end of the housing;
a second spacer between the bottom cover plate and the piezoelectric bimorph layer at the second end of the housing;
a spacer rod connected to the first spacer and a spring connected to the first spacer and extending along the spacer rod;
a spacer connected to the spring, the spacer movable along the spacer rod, the spacer movable between an uncompressed state and a compressed state; and
wherein in the compressed state, the piezoelectric bimorph layer bends downward toward the bottom cover plate, generating a charge stored in an electronics board at the bottom cover plate; and
wherein power consumption by the electronics board is substantially similar to energy corresponding to the charge generated when moving the spacer from the uncompressed state to the compressed state.

9. The thin card reader of claim 8, wherein the electronics board is configured to transmit and receive a wireless protocol.

10. The thin card reader of claim 9, wherein the wireless protocol is NFC (Near Field Communications).

11. The thin card reader of claim 9, wherein the wireless protocol is Bluetooth radio frequency (RF) link.

12. The thin card reader of claim 8, wherein the slot is configured to receive a credit card.

13. The thin card reader of claim 12, wherein the electronics board is configured to retrieve card data from an EMV chip from the credit card.

14. The thin card reader of claim 13, wherein the electronics board is configured to transmit the card data via a wireless protocol.

15. The thin card reader of claim 12, wherein the credit card comprises a biometric sensor.

16. The thin card reader of claim 15, wherein the electronics board is configured to retrieve biometric sensor data from the biometric sensor.

17. The thin card reader of claim 16, wherein the electronics board is configured to transmit the biometric sensor data via a wireless protocol.

18. The thin card reader of claim 16, wherein the electronics board is configured to encrypt the biometric sensor data.

19. The thin card reader of claim 12, wherein the electronics board activates an enrollment mode representing a new credit card when the credit card has not been initialized.

20. A thin card reader, comprising:
a housing having a top cover plate connected to a bottom cover plate, the housing having a first end with a slot extending therethrough and into the housing;
wherein the slot is configured to receive a credit card;
a piezoelectric bimorph layer extending from a second end of the housing between the top cover plate and the bottom cover plate;
a first spacer between the top cover plate and the piezoelectric bimorph layer at the second end of the housing;
a second spacer between the bottom cover plate and the piezoelectric bimorph layer at the second end of the housing;
a spacer rod connected to the first spacer and a spring connected to the first spacer and extending along the spacer rod;
a spacer connected to the spring, the spacer movable along the spacer rod, the spacer movable between an uncompressed state and a compressed state;
wherein in the compressed state, the piezoelectric bimorph layer bends downward toward the bottom cover plate, generating a charge stored in an electronics board at the bottom cover plate; and
wherein the electronics board activates an enrollment mode representing a new credit card when the credit card has not been initialized.

* * * * *